United States Patent [19]

Stocker

[11] Patent Number: 4,837,151
[45] Date of Patent: * Jun. 6, 1989

[54] LIVE VACCINES COMPRISING TWO MUTATIONS AND FOREIGN ANTIGEN

[75] Inventor: Bruce A. D. Stocker, Portola Valley, Calif.

[73] Assignee: The Board of Trustees of the Leland Stanford Junior University, Stanford University, Stanford, Calif.

[*] Notice: The portion of the term of this patent subsequent to Apr. 5, 2005 has been disclaimed.

[21] Appl. No.: 798,052

[22] Filed: Nov. 14, 1985

Related U.S. Application Data

[63] Continuation-in-part of Ser. No. 675,381, Nov. 27, 1984, Pat. No. 4,735,801, which is a continuation-in-part of Ser. No. 415,291, Sep. 7, 1982, Pat. No. 4,550,081, which is a continuation-in-part of Ser. No. 151,002, May 19, 1980, abandoned.

[51] Int. Cl.[4] .................... C12N 15/00; A61K 39/12; C12R 1/42
[52] U.S. Cl. .................................. 435/172.3; 424/87; 424/92; 435/172.1; 435/245; 435/879; 435/252.3; 935/1; 935/9; 935/31; 935/58; 935/65; 935/72
[58] Field of Search ................. 424/87, 92; 935/172.1, 935/172.3, 245, 253, 879; 935/1, 9, 31, 58, 65, 72

[56] References Cited

U.S. PATENT DOCUMENTS 4,337,314  6/1982  Oeschger et al. ................ 435/172.1

OTHER PUBLICATIONS

Yancey, Infection and Immunity, vol. 24, 1974 (1979).
Morris et al, Brit. J. Exp. Path., vol. 57: 354 (1976).
Kleckner et al, J. Mol. Biol., vol. 116, 125 (1977).
Kleckner et al, J. Mol. Biol., vol. 127, 89 (1977).
Kleckner et al. Genetics, vol. 90:427–464 (1978).
Brock et al, Biology of Microorganisms, 1970 pp. 304–307, Prentice-Hall, NJ.

Primary Examiner—Christine M. Nucker
Attorney, Agent, or Firm—Bertram I. Rowland; Barbara Rae-Venter

[57] ABSTRACT

Live vaccines are provided and methods for preparing the live vaccines for protection of a host from a pathogenic microorganism. The vaccines are prepared by introducing at least one modification in a gene involved in at least one, normally at least two, biosynthetic pathways, involving the production of products which are unlikely to be found in the disease susceptible host. The modification results in a gene change which cannot be repaired by a single step e.g. polynucleotide deletions and inversions. Where the aro gene suffers such a change, the resultant auxotrophic mutants require aromatic amino acids, p-aminobenzoic acid and 2,3-dihydroxybenzoic acid or a highly concentrated source of absorbable iron. The auxotrophic mutations have substantially reduced or nonexistent virulence, while retaining the desired immunogenicity to initiate the immunogenic response. Various techniques can be employed for providing the desired change.

*Salmonella typhimurium* strain SL1479 was deposited at the ATCC on Sept. 7, 1982 and given ATCC Accession No. 39183; *Salmonella dublin* strain SL1438 was deposited on Sept. 7, 1982 at the ATCC and given ATCC Accession No. 39184. *Salmonella typhi* strain 531Ty was deposited at the ASTCC on Nov. 21, 1984, and granted ATCC Accession No. 39926.

16 Claims, No Drawings

LIVE VACCINES COMPRISING TWO MUTATIONS AND FOREIGN ANTIGEN

CROSS-REFERENCE TO RELATED APPLICATIONS

This application is a continuation-in-part of U.S. Ser. No. 675,382, filed Nov. 27, 1984, now U.S. Pat. No. 4,735,801, which is a continuation-in-part of U.S. Ser. No. 415,291, filed Sept. 7, 1982, now U.S. Pat. No 4,550,081, issued Oct. 29. 1985, which is a continuation-in-part of U.S. Ser. No. 151,002, filed May 19, 1980, now abandoned, which disclosures are incorporated herein by reference.

BACKGROUND OF THE INVENTION

1. Field of the Invention

Vaccination with live attenuated strains is extensively and successfully used in the prevention of various viral diseases of man, such as polio, smallpox, and measles. By contrast, live vaccines are used against only a few bacterial diseases of man or domestic animals: BCG vaccine for prevention of tuberculosis, strain 19 vaccine against bovine brucellosis and Sterne's spore vaccine against anthrax in cattle. Yet in many investigations of experimental Salmonella infections live vaccines have shown advantages over killed vaccines: (i) They frequently prevent, rather than merely postpone, multiplication of Salmonella in liver and spleen, which multiplication may lead to death; (ii) they provide good protection against challenge by oral route, in situations where killed vaccines, given by injection or orally, are relatively ineffective; (iii) in some instances injections of live vaccine confer ability to rapidly eliminate challenge bacteria from liver, spleen, etc., presumably through cell-mediated immunity, in contrast to killed vaccines which evoke mainly humoral immunity, without much ability to eliminate virulent bacteria. The use of live Salmonella vaccines, however, is hampered by a number of factors. Some strains considered for use as live vaccines retain an unacceptable degree of virulence, by reversion or otherwise. Some live vaccines display short persistence of immunity attributed to early disappearance of the vaccine strain from host tissues and, in some instances, incomplete immunity so that some vaccinated animals die after a large challenge inoculum of a virulent strain.

The non-virulent strains used as vaccines have been obtained in various ways. The BCG strain was derived by empirical procedures during prolonged in vitro cultivation, and probably owes its non-virulence to multiple unidentified mutations. Sterne's *Bacillus anthracis* spore vaccine is a strain which has lost the ability to syntheisze the polypeptide capsule, important as a determinant of virulence but not as a "protective" antigen. Some experimenters have used as live vaccine merely a sublethal dose of a "wild" strain of relatively low virulence in the sense that the LD50 was a large number of bacteria—a situation in which there is evident risk of severe of fatal infection developing in some vaccinated subjects and of transmission to other hosts.

Recently, bacterial strains have been developed for use as live vaccines which are streptomycin-dependent mutants of strains of several pathogenic species. *Shigella flexneri* and *Shigella sonnei* streptomycin-dependent mutants have been extensively used as live vaccines given by mouth for protection and have been to be both safe and efficient. In experimental Salmonella infections, however, streptomycin-dependent mutants seem to have been only moderately satisfactory. In general "rough" mutants in Gram-negative bacterial species, i.e., mutants unable to manufacture normal lipopolysaccharide are non-virulent but have proven unsatisfactory as live vaccines because of failure to cause protection. Two exceptions may be noted. (i) In Salmonella mutation of gene galE prevents normal lipopolysaccharide synthesis unless the bacteria are provided with preformed galactose. A galE mutant of *S. typhimurium* was virtually non-virulent in small laboratory animals but evoked good immunity. As anti-O antibodies were produced the galE bacteria must have obtained sufficient galactose within the host tissue for them to make at least some O-specific lipopolysaccharide. Recently a galE mutant of *S. typhi*, given by feeding to human volunteers, proved non-virulent and conferred reasonable protection against later oral challenge with a virulent strain of the same species. Furthermore, first reports of a field trial of this strain, given by oral route to school children in Alexandria, Egypt, indicate that it gave very good protection against the risk of contracting typhoid fever, which has a high incidence in such children. The non-virulence of galE strains seems to be conditional on the presence of normal host cellular defense mechanisms, since administration of the cytotoxic agent cyclophosphamide to mice previously injected with a galE mutant of *S. typhimurium*, non-pathogenic to untreated animals, precipitated fatal infections due to multiplication of the galE strain. (ii) A "rough" mutant of *S. dublin* is in routine use in Great Britain as a live vaccine, given by parenteral injection, for protection of newborn calves against the frequently fatal Salmonella infections which were formerly prevalent; as the strain used appears to lack the 0-specific part of lipopolysaccharide, it presumably acts by invoking "non-specific immunity," perhaps by causing activation of macrophages.

Since live vaccines have substantially greater probability of success in providing for protection for the host against a subsequent invasion of a virulent wild strain, it is desirable to develop new live vaccines which avoid the shortcomings of vaccines prepared previously. Because the immune response of the vertebrate host to antigens, in particular surface antigens, of the pathogenic microorganism is the basic mechanism of protection by vaccination a live vaccine should retain the antigenic complement of the wild-type strain. The live vaccine should be non-virulent, substantially incapable of multiplication in the host, and should have substantially no probability for reverting to a virulent wild strain.

A non-virulent live vaccine may also serve as a host for the expression of antigens which may be located in the cytoplasm, translocated to the plasma or outer membrane or secreted to provide immunogens for an immunogenic response by the mammalian host. By employing a live vaccine as a carrier for an immunogen, particularly an invasive host, such as *Salmonella typhi*, a strong stimulus can be provided to the immune system, particularly to the humoral immune system. In this way many of the benefits of employing attenuated live pathogens, such as bacteria, fungi, protozoa and viruses can be achieved without concern for reversion to a virulent form.

2. Brief Description of the Prior Art

Sandhu et al., *Infection and Immunity* (1976) 13, 527 describes loss of virulence of *Asperigillus fumigatus* in a mutant auxotroph for p-aminobenzoic acid. Morris et al. *Brit. J. Exptl. Path.* (1976) 57:354 describes the effect of T and B lymphocyte depletion on the protection of mice vaccinated with a galE mutant of *Salmonella typhimurium.* Lyman et al., *Inf. Imm.* (1977) 15:491 compared the virulence of O:9,12 and O:4,5,12 *S. typhimurium* his+ transductants for mice. Descriptions of use of translocatable elements for causing deletions or inversions may be found in Kleckner, et al., J. Mol. Biol. (1977) 116, 125; Kleckner et al., ibid 127, 89; and Kleckner et al., Genetics, 90:427–464 (1978). U.S. Pat. No. 4,337,314 to Oeschger et al. describes the preparation of live *H. influenzae* vaccine strains by combining random mutations in a single strain. Hoiseth and Stocker, *J. Bacteriol.* (1985) 163:355–361, describe the relationship of aroA and serC genes of *S. typhimurium.*

In a private communication, Dr. John Roth, Department of Biology, University of Utah, developed two strains of *S. typhimurium* LT2, in each of which the transposon Tn10, conferring resistance to tetracycline, had been inserted into a gene of the aromatic biosynthetic pathway, thereby causing inability to synthesize the common precursor of the aromatic amino acids and of two bacterial metabolites, p-aminobenzoate, (precursor of the essential metabolite folic acid) and dihydroxybenzoate (precursor of the iron-chelating compound enterochelin or enterobactin). R. J. Yancey (1979) Infection and Immunity, 24, 174 report that a mutation causing inability to synthesize enterochelin secured in a mouse-virulent strain of *S. typhimurium* caused a very considerable reduction in virulence. The metabolic block was between chorismic acid and enterobactin, so that the mutation did not cause the requirement for p-aminobenzoate. In May, 1979, a paper was presented by Stocker and Hoiseth, entitled Effect of Genetic Defects in Iron Assimilation on Aromatic Biosynthesis on Virulence of *Salmonella typhimurium.*

SUMMARY OF THE INVENTION

Live vaccines are provided for vaccinating a host against a pathogenic microorganism, particularly bacteria, as well as serving as carriers for immunogens of other pathogens, particularly microorganisms, including viruses, prokaryotes and eukaryotes. The live vaccines are prepared by producing auxotrophic mutants of a pathogenic strain, wherein normally at least one, usually two or more, biosynthetic pathways are blocked, so that the bacterial mutant requires for proliferation at least one and preferably two or more nutrients which are normally not available in the host in the amount required by the microorganism.

The auxotrophic mutation is a result of a genetic change in a structural gene, which change cannot be repaired by any single step. Such genetic changes include deletion and/or inversion of a polynucleotide segment of the gene, particularly where an inversion occurs immediately adjacent to an inserted foreign nucleotide sequence in the gene. For the purposes of the invention, these changes will be referred to as "non-reverting mutations." Normally, the non-reverting mutation will not affect the antigenic constitution of the pathogenic microorganism, and, in particular, will not alter its surface antigens, some of which may be important determinants of pathogenicity. The resulting auxotrophic mutants have substantially zero probability of reversion, while having the same, or substantially the same, immunogenic characteristics as the virulent strain, so as to produce an effective immunogenic response.

In particular, auxotrophic mutants are obtained by employing a virulent strain, desirably having a genetic marker allowing its selection and creating at least one non-reverting mutation in one or more gene(s), so as to produce a complete block in biosynthesis of one or more essential metabolite(s) which are not normally available in vertebrate tissues. By isolating the mutant and screening for inability to revert, lack of virulence and immunizing ability when used as live vaccines, strains useful for live vaccines may be obtained.

DESCRIPTION OF THE SPECIFIC EMBODIMENTS

Vaccines prepared from live, non-virulent microorganisms are provided which are particularly useful in vaccinating vertebrate hosts susceptible to disease from corresponding pathogenic microorganisms. The non-virulent microorganisms, particularly bacteria, can serve as carriers for antigens for other pathogens, so as to produce a multiple immunogenic response and promote humoral and/or cellular protection from two or more pathogens. The microorganisms are auxotrophic, having a non-reverting, non-leaky block in at least one, usually a plurality of biosynthetic pathways causing a requirement for nutrient(s) not available in the animal to be vaccinated in amounts sufficient to allow multiplication of the microorganism. Thus, the vaccine strains may be grown on media supplemented with nutrient(s), and when introduced to the host will continue to live (until eliminated by the host's immune response), but will be unable to proliferate.

The non-reverting block is created by introducing a mutation into a gene encoding an enzyme indispensably needed for a particular step in a biosynthetic pathway. Since the product of the pathway is unavailable in the host to be vaccinated, the microorganism will be unable to proliferate even though it is alive and retains its native antigenic characteristics. The mutation is non-reverting because restoration of normal gene function can occur only by random coincidental occurrence of more than one event, each such event being very infrequent.

In the case of a deletion mutation restoration of genetic information would require many coincidental random nucleotide insertions, in tandem, to restore the lost genetic information. In the case of an insertion plus inversion, restoration of gene function would require coincidence of precise deletion of the inserted sequence and precise re-inversion of the adjacent inverted sequence, each of these events having an exceedingly minute, undetectably low, frequency of occurrence. Thus each of the two sorts of "non-reverting" auxotrophic mutations has a substantially zero probability of reverting to prototrophy.

While a single non-reverting block provides a high degree of security against possible reversion to virulence, there still remain events which, while unlikely, have a finite probability of occurrence. Opportunities for reversion exist where microorganisms exist in the host which may transfer by conjugation the genetic capability to the non-virulent organism. Alternatively, there may be a cryptic alternative biosynthetic pathway which by rare mutation or under stress could become operative. Thirdly, a nutrient administered to the host may serve as the necessary metabolite resulting in pathogen proliferation and virulence. It is therefore of some interest to develop live microorganism vaccines with two separate and unrelated pathway blocks, which will be viable and reasonably long lived in the host, provide a strong immune response upon administration to the host, and serve as a carrier for antigens of other pathogens to provide immune protection from such pathogens.

In addition to the auxotrophic mutations which prevent multiplication in the vaccinated animal, it is desirable that the microorganism for use as live vaccine have one or more genetic "marker characters" making it easily distinguishable from other microorganisms of the same species, either wild strains or other live vaccine strains. Conveniently, the marker may be a nutritional requirement, such as a histidine requirement. Such markers are useful in distinguishing the vaccine strain from wild type strains, particularly when a vaccinated patient succumbs to Salmonella infection as a result of exposure before the vaccine immunity had been established.

After manipulating the microorganism so as to introduce one or more non-reverting mutations into some members of the population the microorganisms are grown under conditions facilitating isolation of the auxotrophic mutants, either under conditions under which such mutants have a selective advantage over parental bacteria or under conditions allowing their easy recognition from unaltered bacteria or mutants of other types. The isolated auxotrophic mutants are cloned and screened for virulence, inability to revert and ability to protect the host from a virulent pathogenic strain.

The subject method for preparing the vaccines and the vaccines have a large number of advantages over prior vaccines. As contrasted with other vaccines, the subject invention provides for the exact cause of the loss of virulence. Unlike other live vaccine strains which are non-virulent because of alteration of lipopolysaccharide character, the subject vaccines will be substantially unaltered in 0 antigenic character, as well as other surface antigens which may have relevance to virulence and immunity, such as the major outer membrane proteins. Thus, the subject vaccines would stimulate production of anti-0 antibodies which are known to be important components in the immunity obtainable by vaccination. The subject strains should be able to persist in the host for extended periods of time, usually weeks, to enhance the effectiveness of the immunizing effect by continuous stimulation of the host immune system until the host immune system has cleared all the organisms. The auxotrophic mutants having non-reverting, non-leaky mutations will have substantially zero likelihood of reverting to virulence. In view of the fact that the non-virulence depends upon the absence of relevant metabolites in host tissues and not on any host cellular function, the subject strains will be non-virulent even in immunodeficient hosts.

Among bacteria, the subject invention is particularly applicable to a wide variety of Salmonella strains, more particularly of groups A, B, or D, which includes most species which are specific pathogens of particular vertebrate hosts. Illustrative of the Salmonella causing disease for which live vaccines can be produced are *S. typhimurium; S. typhi; S. abortus-ovi; S. abortus-equi; S. dublin; S. gallinarum; S. pullorum;* as well as others which are known or may be discovered to cause infections in mammals.

Other organisms for which the subject invention may also be employed include Shigella, particularly *S. flexneri* and *S. sonnei;* Haemophilus, particularly *H. influenzae,* more particularly type b; Bordetella, particularly *B. pertussis;* Neisseria, particularly *N. meningitidis* and *N. gonorrhoeae;* Pasteuralla, particularly *P. multocida* and Yersinia, particularly *Y. pestis.*

The vaccines can be used with a wide variety of domestic animals, as well as man. Included among domestic animals which are treated by vaccines today or could be treated, if susceptible to bacterial diseases, are chickens, cows, pigs, horses, goats, and sheep, to name the more important domestic animals.

In preparing the live vaccines, one chooses a strain of the pathogen which desirably has a marker for distinguishing the auxotrophic mutant to be produced from other members of the strain. Alternatively, such a marker can be introduced into the vaccine strain. Various markers can be employed, such as resistance to antibiotic or synthetic antibacterial drug, a block in a biosynthetic pathway causing requirement for an amino acid, e.g., histidine, or the like. The limitation on the particular marker is that it should not affect the immunogenic character of the microorganism, nor should it interfere with the processing of the microorganism to produce the live vaccine. The marker will alter the phenotype, to allow for recognition of the subject microorganism.

The subject organism will then be processed to provide one or more non-reverting mutations. Each non-reverting mutation will involve a polynucleotide of greater than five nucleotides, more preferably a polynucleotide of at least ten nucleotides, and will block at least one, preferably a plurality of biosynthetic pathways, normally two or more. The mutations may be deletions, insertions, or inversions, or combinations thereof. The blocked biosynthetic pathways should not be involved in the production of the antigens involved with the microorganisms' virulence, nor the host's immune response to infection by the microorganism. Various techniques can be employed for introducing deletions or insertion inversions, so as to achieve a microorganism having the desired "non-leaky" non-reverting biosynthetic pathway blocks.

The choice of gene will be governed by the ability to mutate the gene without destroying the viability of the microorganism; the essential nature of the product expressed by the gene; and the unlikely presence of the product in the intended host. The blocked gene must prevent production of an enzyme required in the biosynthetic pathway of a metabolite necessary for multiplication, but not otherwise necessary for viability. Genes of particular interest include several of the aro genes; pab which is involved in the production of p-aminobenzoic acid; and the pur genes which are involved in the conversion of inosinemonophosphate to adenosinemonophosphate, causing requirement for adenine or an adenine compound.

One technique for producing a non-reverting biosynthetic pathway block is the employment of translocatable elements, in particular transposons. Transposons are segments of double-stranded DNA, made up of some thousands of nucleotides, and normally comprising a gene for resistance to an antibiotic or other antibacterial drug; together with genes which can effect the insertion of a copy of the transposon at any of very many different sites in the DNA of the bacterium housing the transposon. Insertion of a transposon into a gene which specifies the amino acid sequence of an enzymically active protein causes complete loss of ability to synthesize that protein in active form. However the whole transposon is, at a low frequency (for instance, $10^{-8}$/bacterium/generation) deleted or excised from the gene into which it was inserted, this gene in consequence being restored to its original state, so that it again specifies an enzymically active protein. Such precise excision of a transposon causes loss of the resistance to the antibiotic or other antibacterial agent, which resulted from the action of the resistance gene of the transposon.

In addition to precise excision, loss of resistance conferred by the transposon occurs also by other kinds of events, which are much more frequent than precise excision and do not result in reconstitution of the original form of the gene, thus not resulting in restoration of the lost gene function. Two kinds of such event result in production of a non-reverting non-functional form of the gene into which the transposon was inserted: one event is deletion of a segment of DNA comprising the whole or a part of the transposon, including its resistance gene, and a segment of DNA extending to one side of the site of insertion, thus extending into, sometimes entirely through, part of the gene into which the transposon was inserted, to one side of the site of insertion; the other event is deletion of a part of the transposon and simultaneous inversion of a DNA segment which includes genetic material extending to one side from the site of the original insertion, i.e., part or the whole of the portion of the affected gene to one side of the site of the original insertion. Restoration of the affected gene to its original state can then occur only by precise deletion of the remaining part of the transposon together with re-inversion of exactly the inverted DNA segment, i.e., by the coincidental occurrence of two events each of which is expected to be exceedingly infrequent, probably undetectably rare.

The consequence of either of these two kinds of event, deletion or deletion plus inversion, occurring in a bacterium with a transposon insertion in a gene specifying a biosynthetic enzyme is to change the transposon containing antibiotic-resistant auxotrophic bacterium with a genetic lesion causing an enzyme defect, which though complete is liable to rare reversion, to an antibiotic-sensitive bacterium with the same enzyme defect, as before, absent the intact transposon, and now no longer subject to correction by rare reversion events. Thus when the transposon is inserted into a gene specifying an enzyme used in a biosynthetic pathway leading to a metabolite or metabolites essential to the bacterium for multiplication but nonavailable in its vertebrate host, the final result is a bacterial strain with a complete and non-reverting mutation causing non-virulence.

Isolation of auxotrophic mutants can be facilitated by use of penicillin, to kill non-auxotrophic bacteria and so increase the proportion of nutritionally exacting mutants in the population. Once a mutant with the desired auxotrophic character has been isolated a large population of the mutant can be screened for presence of any descendants able to grow without the relevant metabolite, thus testing the probability of reversion of the mutation; this test is made more rigorous if the population is first exposed to a mutagenic agent, or agents, capable of inducing a wide variety of mutational changes, i.e., base substitutions, frameshifts, etc. Furthermore if a recombination system is available, a mutant with a deletion of a segment of a gene covering the sites of two or more point mutants can be recognized by the absence of wild-type recombinants, when the deletion mutant is crossed with each of the point mutants in question. In these ways one can assure that the auxotrophic mutant investigated is almost certainly a result of deletion, rather than of point mutation.

A general transducing phage, such as phage P1, able to adsorb to bacteria of a wide range of genera (if necessary after appropriate genetic modification of their lipopolysaccharide character, to provide the necessary ability to adsorb this phage) can be used to transduce a non-functional biosynthetic gene, such as an aro or pur gene inactivated by insertion of a transposon or otherwise, from its original host to a pathogenic bacterial strain of a different species or genus, wherein it will have some probability of incorporation into the chromosome, there replacing the homologous wild-type gene, to produce an auxotrophic transductant. However, the frequency of such replacement is likely to be much reduced by the incomplete base-sequence homology of corresponding genes in bacteria of different genera. DNA-mediated transformation or bacterial conjugation can similarly be used to transfer an aro, pur or other biosynthetic gene inactivated by transposon insertion or otherwise into bacteria of species or genera different from that of the original strain, to yield auxotrophic bacteria now non-virulent because of requirement for a metabolite not available in vertebrate host, and unable to revert to prototrophy due to the presence of either a deletion or insertion-inversion.

Conjugation may also be employed involving conjugational crossing of a virulent strain with a non-virulent but amenable strain having the desired non-reverting mutated gene. By employing an Hfr or F+ strain with an F− virulent strain, transfer of the mutated gene to the virulent strain can occur with recombination resulting in the replacement of the wild gene by the mutated gene. One would then select for the auxotroph as described previously.

The use of a transducing phage, DNA-mediated transformation, and/or conjugation may also be employed to successively introduce two or more independently mutated genes into a single host strain to be used as the vaccine. The presence of two completely independent mutations, each of which has an extremely low probability of reversion, provides almost absolute assurance that the vaccine strain cannot become virulent. In the Experimental section, the construction of two such double mutations (aroA$^-$, purA$^-$) using transducing phage P22 to transfer the independent mutations is described.

In accordance with the subject invention, the vaccines are produced by introducing a non-reverting mutation in at least one gene, where each mutation is of a sufficient number of bases in tandem to insure a substantially zero probability of reversion and assurance of the non-expression of each mutated gene, in the sense of its total inability to determine production of an enzymically active protein. In addition, each gene chosen will be involved in at least one, and preferably at least two biosynthetic pathways to produce metabolites which are either infrequently present in the host or completely absent. The type of gene and number chosen will result in the likelihood that a host for the vaccine will provide the necessary nutrients for proliferation will have a probability approximating zero. These requirements have been shown to be fulfilled by the aroA and purA genes of Salmonella, particularly *typhimurium dublin* and *typhi*, so that these genes are preferred, although other genes, as previously indicated, may also serve as the site for the non-reverting mutation.

In the case of transduction, the transposon has a marker which allows for selection of the transduced microorganism. For example, if the transposon provides resistance to a biostat or biocide e.g. antibiotic, by growing the transduced microorganism in a nutrient medium containing the bioactive agent, one selects for the transductant strain. One can then employ other techniques, as will be described below, to select for members of the transductant strain which undergo excision of all or part of the transposon where the transposon carries with it a portion of the gene into which it had been integrated or results in an inversion of a portion of the gene.

In order to isolate the auxotrophic strain, whether produced by transduction, mutagenesis, transformation or other means, it is desirable to provide selective pressure to the treated virulent strain to enhance the proportion of the desired auxotrophic strain. One technique is to employ a drug, e.g. a pencillin, which is only lethal to bacteria which are multiplying. By employing a nutrient medium which does not provide one or more of the metabolic products required by the auxotrophic strain due to the mutation introduced above, the auxotrophic strain will be inhibited from multiplying, while the virulent parent strain will multiply and so be killed by the pencillin. Normally, at least about 99% of the bacteria are killed and less than 100%, so that the surviving about 0.05 to 1% of the original bacteria have a greatly enhanced concentration of the auxotrophic strain. One can then grow the surviving bacteria in a supplemented medium which will allow for multiplication of the auxotrophic strain and repeat the penicillin killing process until one can isolate the auxotroph from a single colony and establish the complete absence of any of the virulent parent strain.

The resulting auxotrophic strain will be a non-virulent live vaccine, having the desired immunogenicity, in that the deletion will not affect the production of the antigens which trigger the natural immune response of the host. At the same time, the deletion results in a non-virulent live vaccine, incapable of growing in the host and incapable of reverting to a virulent strain.

Two particularly valuable strains having aroA deletion were prepared generally as follows. A characterized Salmonella strain was exposed to a transducing phage grown on a different Salmonella strain which was aroA554::Tn10 and selection made for increased resistance to tetracycline. Tetracycline resistant aromatic-dependent transductants were incubated on Bochner medium. Mutants growing well on this medium were then picked and screened for inability to revert to aromatic independence, indicating a deletion or deletion-inversion mutation in aroA. The transductants may be screened employing mice and a strain which is non-virulent and provides protection against inoculation with a virulent strain selected. As a matter of convenience, one may introduce a marker, for example, auxotrophy, to provide a specific nutritional requirement, which then allows a rapid determination of contracts Salmonella at the time of a subsequent vaccination with the vaccine prepared in accordance with this invention. The construction of aroA$^-$, purA$^-$ Salmonella strains is also described in the Experimental section.

To provide for antigens of species other than the non-virulent host, one or more genes coding for the desired antigens may be introduced into the host as expression cassettes, or for enzymes for synthesis of the desired antigen(s). By expression cassette is intended transcriptional and translational initiation and termination regions bordering the structural gene of interest with the structural gene under the regulatory control of such regions, that is, properly spaced and being 5' and 3' to the structural gene, respectively. Where bacterial or bacteriophage structural genes are involved, the natural or wild-type regulatory regions will usually, but not always, suffice. With structural genes from eukaryotes (including viruses) and occasionally with prokaryotes, the structural gene will be joined to regulatory regions recognized by the bacterial host.

The expression cassette may be a construct or may be or form part of a naturally-occurring plasmid such as the plasmid encoding the enzymes for production of the O-specific part of the LPS of *Shigella sonnei.* If the expression cassette is a construct, it may be joined to a replication system for episomal maintenance or may be introduced into the bacterium under conditions for recombination and integration. The construct will normally be joined to a marker, e.g., a structural gene and regulatory regions providing for antibiotic resistance or complementation in an auxotrophic host, so that the expression vector will usually include a replication system, e.g., plasmid or viral, one or more markers and the expression cassette of the structural gene of interest.

Structural genes of interest may come from diverse sources, such as bacteria, viruses, fungi, protozoa, metazoan parasites or the like. The structural genes may encode envelope proteins, capsid proteins, surface proteins, toxins, such as exotoxins or enterotoxins, or the genes of interest may specify proteins, enzymes or other proteins, needed for synthesis of a polysaccharide or olygosaccharide antigen or for modification of a saccharide containing antigen, such as LPS, of the host bacterial strain, or for synthesis of a polypeptide antigen, such as the capsular antigen of *Bacillus anthrais.* These genes may be isolated in conventional ways employing probes where at least a partial amino acid or nucleic acid sequence is known, using Western blots for detection of expression, using λgtll for expression of fused proteins for obtaining probes, identification of the antigen by reaction of transconjugant bacterial colonies with antibody and detecting complex formation, e.g., agglutination, etc.

Specific genes of interest include those specifying the heat-labile and heat-stable enterotoxins of enterotoxigenic *E. coli* or *Vibrio cholerae* strains, HBsAg, surface, envelope or capsid proteins of *T. cruzi, B. pertussis,* Streptococci, e.g., *S. pneumoniae,* Haemophilus, e.g., *H. influenzae, Nersseria,* e.g., *N. meningitidis,* Pseudomonas, e.g., *P. aeruginosa,* Pasteurella, Yersinia, Chlamydia, Rickettsiae, adenovirus, astrovirus, arenavirus, coronavirus, herpes virus, myxovirus, paramyxovirus, papovavirus, parvovirus, picornavirus, poxvirus, reovirus, retrovirus, rhabdovirus, rotavirus, togavirus, etc; the genes specifying the enzymes needed for synthesis of polysaccharide antigens, e.g., Meningococcus capsular polysaccharide, or for modification of the oligo- or polysaccharide antigen of the bacterial host strain.

The construct or vector may be introduced into the host strain by any convenient means such as conjugation, e.g., F+ *or hfr strain, transformation e.g., Ca precipitated DNA,*

*transfection, transduction, etc. Modified hosts may then be selected on selective medium employing the phenotype of the marker.*

The subject vaccines may be used in a wide variety of vertebrates. The subject vaccines will find particular use with mammals, such as man, and domestic animals. Domestic animals include bovine, ovine, porcine, equine, caprine, domestic fowl, Leporidate e.g., rabbits, or other animal which may be held in captivity or may be a vector for a disease affecting a domestic vertebrate.

The manner of application of the vaccine may be varied widely, any of the conventional methods for administering a live vaccine being applicable. These include oral application, on a solid physiologically acceptable base, or in a physiologically acceptable dispersion, parenterally, by injection, or the like. The dosage of the vaccine (number of bacteria, number of administrations) will depend on route of administration and will vary according to the species to be protected. For mice, of weight 15–20 g, a single dose of ca. $3 \times 10^5$ live bacteria of a non-reverting aro$^-$ vaccine strain of *S. typhimurium*, given in a volume of 0.2 ml in saline by intraperitoneal injection, appears both safe and effective, as judged by the result of later parenteral challenge with virulent *S. typhimurium*. Mice have also been given ca. $3 \times 10^7$ live bacteria of the same strain, in bread cubes moistened with 0.1 ml of broth culture, provided after six hours deprivation of other food. This dose proved harmless and was found to provide immune protection. Observations on vaccinated calves suggest that administration of live bacteria of the same strain, by intramuscular injection or by feeding, in doses a thousandfold greater than used for mice are safe, and may be appropriate. One or more additional administrations may be provided as booster doses, usually at convenient intervals, such as two to three weeks.

The formulations for the live vaccines may be varied widely, desirably the formulation providing an enhanced immunogenic response. The live vaccine may be provided on a sugar or bread cube, in buffered saline, in a physiologically acceptable oil vehicle, or the like.

The following examples are offered by way of illustration and not by way of limitation.

EXPERIMENTAL

1. Construction of aro$^-$ Strains

A live vaccine derived from a *Salmonella typhimurium* was prepared as follows. As the parent strain, a mouse-virulent *S. typhimurium* SL4522 was employed which is a descendant of a "wild" *S. typhimurium* strain M7471 of the *S. typhimurium* subgroup called FIRN (Morgenroth and Duguid, Gent. Res. (1968), 11:151–169). This subgroup is defined by its inability to ferment rhamnose or inositol and failure to product type 1 pili or fimbriae. Strain M7471 was given a colicin factor or plasmid, ColE1-K30, by conjugation, then made, by successive exposures to a mutagen, maltose-negative, leucine-requiring and cystine-requiring followed by being made histidine-requiring by transducing in mutation hisC527 (an *amber* mutation). The genetic constitution of the starting strain, SL4522, is thus *S. typhimurium* M7471 (ColE1-K30) malB479 leu-1051 cysI1173 hisC527 (MacPhee et al. J. Gen. Microbiol. (1975) 87:1–10). This strain which retains its mouse virulence was reisolated from a mouse which had died from a small inoculum and the reisolate was designated SL3201.

*S. typhimurium* containing a transposon imparting tetracycline resistance and being present in gene aroA, designated as strain TT1455 and having genetic constitution *S. typhimurium* LT2 aroA554::Tn10, was employed as a source of t on employed in the subject preparation. This strain has been developed and is available from Dr. John Roth, Department of Biology, University of Utah, Salt Lake City and has been deposited at the ATCC with Deposit No. 33275. The insertion site of the transposon Tn10 is in gene aroA, which is located at position 19 on the linkage map and specifies the enzyme 3-enolpyruvylshikimate-5-phosphate synthetase. Strain TT1455 cannot grow on chemically defined media unless provided with the essential metabolites derived from chorismic acid, i.e. the aromatic amino acids tyrosine, phenylalanine, and tryptophan and two minor aromatic metabolites, p-aminobenzoate, needed as a precursor of folic acid, and 2,3-dihydroxybenzoic acid, as a precursor of the iron-chelating compound enterobactin (enterochelin).

For the transduction, a high-transducing mutant, HT105/1 (Schmiger, Mol. Gen. Genet. (1972) 119:75–88) of the general transducing phage P22 was employed having an additional mutation int, hindering lysogenization and facilitating preparation of high-titer phage stocks. In accordance with conventional techniques, this phage was grown on strain TT1455; the resulting lysate, after removal of all bacteria by centifugation was further treated by membrane filtration. A plate of nutrient agar (Oxoid blood agar base No. 2, code CM55) supplemented with tetracycline, (25 $\mu$g/ml) was flood-inoculated with a broth culture of the recipient strain SL3201; drops of the phage lysate, volume approximately 0.01ml, were applied to the plate and the plates were incubated at 37° for about 18 hrs. After incubation, each drop-area showed many large (approximately 2mm diameter) colonies of tetracycline-resistant "complete" transductants (also many very small colonies of abortive transductants), whereas the agar between the drops showed no growth. Two tetracycline-resistant transductant clones were obtained, re-isolated from single colonies and tested to confirm freedom from phage P22, and were then designated strains SL3217 and SL3218. They showed the expected phenotype in requiring for growth provision of tyrosine, phenylalanine, tryptophan, $\delta$-aminobenzoate and 2,3-dihydroxybenzoate. The strains SL3217 and SL3218 showed the expected loss of mouse-virulence, provided that they were grown in the presence of tetracycline, to prevent accumulation of aromatic-independent revertants.

The isolation of tetracycline-sensitive variants is facilitated by the fact that tetracycline, at appropriate concentrations, prevents multiplication of tetracycline-sensitive bacteria, but does not kill them, whereas penicillin kills multiplying bacteria but spares non-multiplying bacteria. The technique of penicillin-selection was used for isolation of tetracycline-sensitive variants from the aroA::Tn10 strain SL3218. The strain was first grown in broth, without tetracycline to a concentration of approximately $9 \times 10^8$ cfu/ml; this culture was then diluted 1:10 into broth containing tetracycline, 5$\mu$g/ml, and the diluted culture incubated at 37° with aeration for 75 min; ampicillin, 2.5$\mu$g/ml, was added and incubation with shaking was continued for 290min; the culture was then held at room temperature without shaking overnight. Surviving bacteria were washed on a membrane filter to remove ampicillin, and then plated on an indicator medium containing dyes and a very low concentration of tetracycline. On this medium, tetracycline-sensitive bacteria produce small, dark colonies, whereas tetracycline-resistant bacteria produce large pale colonies. The ampicillin treatment reduced the number of viable bacteria by about $10^{-5}$. Six of 386 survivor colonies tested proved to be tetracycline-sensitive. Two such isolants, designated SL3235 and SL3236 were shown to resemble their parent strain SL3218 in nutritional character, but to differ from it not only by their tetracycline-sensitivity, but also by their failure to produce any aromatic independent revertants, in tests which would have detected reversion at a frequency of one in $10^{11}$/bacterium/generation. One of these strains, SL3235, when used as live vaccine in mice and calves, showed no reversion to aromatic-independence of virulence. Another non-reverting aro$^-$ vaccine strain was prepared from S2357/65, a *Salmonella typhimurium* strain known from experiments elsewhere to be highly virulent for calves. Strain S2357/65 is prototrophic: to provide a marker character it was made by transduction first hisD8557::Tn10 (therefore phenotypically with a histidine requirement not satisfied by histidinol, and tetracycline-resistant), then by a second transduction made hisD+ hisG46 (thus phenotypically with requirement for histidine or histidinol, and tetracycline-sensitive). This derivative, SL1323, was shown to cause fatal infection when fed to a calf. The calf-passage strain, labeled SL1344, was next made aroA544::Tn10 by transduction from TT1455, as described above; the hisG46 aroA544::Tn10 strain so obtained was labeled SL1346. A tetracycline-sensitive mutant, still aromatic-requiring but now unable to revert to aromatic independence, was next isolated from SL1346 by a new method, i.e., selection on nutrient agar containing chlortetracycline, 50 μg/ml, added before autoclaving, and fusaric acid, 12 μg/ml, added after autoclaving. This medium prevents or at least greatly retards growth of tetracycline-resistant bacteria but allows good growth of tetracycline-sensitive bacteria. Both this strain and two aroA:Tn10 strains, SL3217 and SL3218 grown with tetracycline, to prevent accumulation of tetracycline-sensitive aro+, therefore virulent, revertants have been shown to be effective as live vaccine when administered to mice by intraperitoneal route. (i) Experiments with strains SL3217 and SL3218: CF1 mice given ca. $2 \times 10^5$ live vaccine-strain bacteria, i.p.: challenge two months later with $2 \times 10^6$ bacteria (i.e. more than 20,000 LD50) of virulent *S. typhimurium* strain SL3201, i.p.: no deaths in two months' observation. (ii) CBA/N×DBA/LN F$_1$ female mice given $10^6$ or $10^5$ live-vaccine strain SL3235, i.p.: challenged five weeks later with $10^6$ bacteria (ca. 100 LD50) of virulent *S. typhimurium* strain TML, i.p.: no deaths in fifteen days' observation. In other experiments the stable aro$^-$ vaccine strain, SL3235, has been shown not to cause death (nor any obvious ill effects) when injected intraperitoneally even into mice exceptionally susceptible to *Salmonella typhimurium* infection, either in consequence of prior intravenous injection of macroparticulate silica, so as to destroy phagocytic function of macrophages, or in mice exceptionally susceptible because of a genetic defect in ability to respond to lipopolysaccharide, i.e., strain C3H/Heg. A non-reverting aromatic-dependent derivative thus obtained, number SL3261, has been shown to be non-virulent for mice and calves, by parenteral or oral routes. In addition, a derivative of type aroA::Tn10, similarly derived by transduction from a calf-virulent strain of the bovine-pathogenic species, *Salmonella dublin*, has been shown to be non-virulent for mice; and aroA::Tn10 derivatives, presumably non-virulent, have been made by transduction from several recently isolated strains of the human pathogen, *Salmonella typhi*.

The aro$^-$ live-vaccine *S. typhimurium* SL1479 was prepared as follows. The parent strain was *S. typhimurium* UCD108-11 (Dr. Bradford Smith, University of California at Davis). A calf-passaged re-isolate of strain UCD108-11 was assigned stock number SL1420 and characterized as being nutritionally non-exacting, resistant to various antibiotics including tetracycline and smooth but resistant to the 0-specific general transducing phages, including P22. Strain SL1420 was exposed to a transducing phage grown on an aroA554:::Tn10 strain of *S. typhimurium* and selection made for increased resistance to tetracycline, by plating on a nutrient agar medium with tetracycline (50mg/ml). Representative transductants of increased tetracycline resistance, aromatic-dependent and unaltered in phage sensitivity pattern were selected and one chosen and designated as strain SL1421. The parent strain grew well on Bochner medium (Bochner et al. (1980) J. Bact. 143:926–933) suggesting that the tetracycline resistance was determined by a mechanism other than the resistance conferred by Tn10. Strain SL1421 grew poorly on Bochner medium allowing for selection of colonies developing on plates of Bochner medium supplemented with dihydroxybenzoic acid. One such variant was found to be aromatic-dependent and unaltered in phage pattern and did not yield aromatic-independent revertants at a detectable frequency (zero yield of Aro+ in a final population of approximately $9 \times 10^{10}$ bacteria on plates of medium with a growth-limiting content of tryptophan). This mutant designated SL152 was tested for virulence. Five BALB/c mice (males, age approximately 18 weeks old) each received about $3.5 \times 10^6$ live bacteria of strain SL1452 by intraperitoneal (i.p.) injection.

The mice used were from a colony of the inbred line BALB/c, Caesarian-derived and barrier-maintained with a defined gut flora, in the Department of Radiology, Stanford University School of Medicine. The mice of this line have known high susceptibility to *S. typhimurium* infection and known inability to be protected against such infection by immunization with heat-killed vaccine (Robson and Vas (1972) J. Infect. Dis. 126:378–386). All survived to day 50 and looked well throughout.

To test the immunizing ability of strain SL1452, the five survivors of i.p. injection were challenged seven weeks after vaccination by i.p. injection of about $5 \times 10^5$ bacteria of strain SL1420 (virulent ancestor strain). Four control mice (not vaccinated) died on days 4, 4, 4, and 5 after challenge. One of the five vaccinated mice died by *S. typhimurium* infection and the other four vaccinated mice survived and looked well to day 14 after challenge.

A genetic "marker" character was then introduced into the vaccine strain SL1452 to allow for identification. Strain SL1452 was treated with a transducing phage grown on an *S. typhimurium* strain carrying hisD8557::Tn10 and selection made for increased tetracycline resistance. Representative transductants were found to be of the expected nutritional character, Aro$^-$ HisD$^-$ (*i.e. a requirement for histidine not satisfied by histidinol*). The selected transductant was designated strain SL1474. This strain was exposed to a transducing phage grown on a hisC527 line of *S. typhimurium* and selection was made on a defined medium with aromatics and with histidinol as the histidine source. Some transductants were still aromatic-dependent and histidine-requiring, but able to use histidinol in place of histidine (i.e. of the nutritional character expected from replacement of hisD::Tn10 hisC+ of the recipient by hisD+ hisC527 the donor). One such transductant numbered SL1479 of constitution UCD108-111 aroA554::Tn10/DI hisC527 was employed for tests in calves (DI-deletion-inversion event).

Ten calves, aged two weeks, were given *S. typhimurium* live vaccine strain SL1479 by intramuscular (i.m.) injection, usually about $1.5 \times 10^9$ live bacteria as their first vaccination. None of them lost appetite or became seriously ill and only one developed diarrhea. None gave a positive stool culture for Salmonella. Three calves, aged two weeks, were given approximately $1.5 \times 10^{11}$ live bacteria of strain SL1479 by mouth as their first vaccination. None of them lost appetite but one developed diarrhea; all three gave positive stool cultures, as expected. Reactions to a second dose of live vaccine, by i.m. or oral route, were no more severe than to the first dose.

To test the protection conferred by vaccination, groups of calves aged five weeks, either non-vaccinated (controls) or vaccinated twice with live *S. typhimurium* SL1479 by by i.m. or oral route, were challenged by oral administration of $1.5 \times 10^{11}$ live bacteria of a calf-virulent *S. typhimurium* strain, usually strain UCD108-111, but some calves were given strain SL1323.

All of 16 challenged control calves showed anorexia and depression; 15 had diarrhea and 14 died. Of seven calves which had had two doses of live vaccine by the i.m. route, three had diarrhea after challenge, two became anorectic and depressed and one died. The differences between control calves and those i.m. vaccinated in respect of death (14 of 16 versus 1 of 7) and of anorexia and depression (16 of 16 versus 2 of 7) are statistically significant (p[probability]—less than 0.001 for each comparison). Of three calves which had had two doses of SL1479 live vaccine by oral route, two had diarrhea after challenge and one was anorectic and depressed; none died. The differences between control and oral-vaccinated calves in respect of deaths (14 of 16 versus 0 of 3) and of anorexia and depression 16 of 16 versus 1 of 3) are statistically significant (p less than 0.01 for each comparison.)

The development of the *S. dublin* strain SL1438 substantially followed the procedure described for the *S. typhimurium* described above. The starting strain *S. dublin* S4454 (Dr. Clifford Wray, Central Veterinary Laboratory of the British Ministry of Agriculture, Weybridge, England) was found to be of the expected nutritional character (i.e. with an incomplete dependence on nicotinic acid, otherwise non-exacting), smooth, but resistant or only slightl sensitive to the general transducing 0-specific phages P22, P22h, KB1 and A3, and sensitive to all tested antibiotics, including tetracycline. The strain was assigned number SL1363 and was shown to be virulent by intraperitoneal injection at $4 \times 10^4$ live bacteria in BALB/c mice.

Strain SL1363 was exposed to transducing phage grown on *S. typhimurium* TT47 of genotype hisD8557::Tn10 and tetracycline-resistant transductants selected A transductant of HisD− nutritional phenotype and of unaltered phage sensitivity pattern was selected and designated SL1365 and exposed to phage grown on *S. typhimurium* strain of genotype hisG46 hisD . Transductants were selected on medium with histidinol as the only histidine source and a transductant selected of unaltered phage pattern and requiring either histidine or histidinol (i.e. hisD+ hisG46) and assigned label SL1367. When three BALB/c mice previously deprived of food for several hours were given about $3 \times 10^7$ bacteria of strain SL1367 on a cube of bread, all three died about seven days later. When the same strain was fed to a calf, it caused a rapidly fatal infection and a re-isolate was shown to be unaltered in nutritional phenotype. Strain SL1372 was then treated with phage grown on an aroA554::Tn10 strain of *S. typhimurium* and selection made for tetracycline resistance. A selected transductant which required aromatic supplements, as well as histidine and nicotinic acid, and had an unaltered phage pattern was designated SL1437. Tetracycline-sensitive mutants of strain SL1437 were selected by incubation on plates of Bochner medium, supplemented with 2,3-dihydroxybenzoic acid, so as to allow synthesis of enterobactin. A tetracycline-sensitive but still Aro− variant was selected and assigned SL1438 and was shown not to produce aromatic-independent revertants at detectable frequency.

Strain SL1438 was given in different amounts to three groups of five mice i.p. from an overnight, 37° C., not-shaken broth culture. None of the vaccinated mice showed any apparent ill effects, even from $3 \times 16^6$ bacteria, the largest dose given.

To test the immunizing ability of strain SL1438, the mice from the above experiment and also a control group of five non-vaccinated mice were challenged 30 days after vaccination by i.p. injection of $3 \times 10^5$ bacteria of strain SL1372 (i.e. the virulent *S. dublin* strain made hisG46, re-isolated from a calf infected by feeding). The results compiled after 93 days of challenge, of the control, 5 of 5 died on days 4, 4, 5, 5 and 6. Of those vaccinated at a level of $3 \times 10^4$, 3 of 5 died on days 5, 8 and 8, and 2 of 5 were sick but recovered. Of those vaccinated at a level of $3 \times 10^5$, 2 of 5 died on days 7 and 13 and 3 of 5 looked sick, but recovered. Of those vaccinated at a level of $3 \times 10^6$ live bacteria of strain SL1438, 0 of 5 died and 5 looked well throughout. At the level of $3 \times 10^6$ live bacteria of strain SL1438, a single i.p. dose was found to protect the highly susceptible strain of BALB/c mice.

Five-week-old calves were then employed, either being vaccinated or non-vaccinated as controls, to test the adequacy of the *S. dublin* strain SL1438 as a live vaccine. Vaccination was by two i.m. doses of $1.5 \times 10^9$ of the bacteria of the subject strain. All the calves were then challenged by administration of $1.5 \times 10^{10}$ bacteria of a calf-virulent *S. dublin* strain SL1367. All three control calves died. None of the five vaccinated calves died.

2. Construction of aro−pur−Strains

Transductional procedure.

Each of the several steps of transduction was effected by use of a "high-transducing" non-lysogenizing derivative of phage P22 (P22 HT105/1 int). This phage was propagated, by standard methods, on the *S. typhimurium* strain used as donor. The lysate used was bacteriologically sterile and had a titer, on P22-sensitive indicator strain *S. typhimurium* SL1027, of $3 \times 10^9$ at least plaque-forming units/ml. Transductants were obtained by the "drop-on-lawn" procedure, where plates of a medium selective for transductant phenotype were inoculated by flooding with a broth culture of the recipient strain, excess fluid was pipetted off, and the surface of the agar was allowed to dry by evaporation. Drops of phage lysate, neat and appropriately diluted, were then applied and allowed to dry, followed by incubation at 37° C.

Tetracycline-resistant transductants were selected on "Oxoid" blood agar base, code CM55, supplemented with 25 μg/ml tetracycline. For recipient strains deficient in aromatic biosynthesis, this medium was supplemented with 2,3-dihydroxybenzoic acid (DBA), to allow synthesis of enterobactin which is required for capture of ferric iron. For selection of transductants of altered nutritional character, a simple defined medium supplemented with tryptophan and cystine (requirements of wild-type S. typhi) was used.

The transduction plates were inspected after 1,2,3 and 4 days of incubation, and colonies appearing in the drop areas were picked and purified by streaking out and selection of discrete colonies, on the same medium as that on which selection was made. In general, transductant colonies developed later, and in much smaller numbers, e.g., by a factor of $10^3$, in crosses in which the recipient was S. typhi, as compared with those in which it was S. typhimurium, like the donor. This presumably resulted from incomplete genetic homology of the genes of the S. typhimurium donor with the corresponding genes of the S. typhi recipient, greatly reducing the frequency of crossing-over events and so of integration of donor genes into recipient chromosome. Purified transductant clones were tested to insure that they were S. typhi, not aerial contaminants, and to confirm that they were of the phenotype being sought.

Introduction of aroA deletion.

Introduction of the aroA deletion was effected by two steps of transduction. In the first step, the parent strain (CDC10-80) was treated with phage lysage G2077, which is phage P22HT 105/1 int grown on S. typhimurium strain TT472, which is aroA(-serC)1121:Tn10. Desired transductants would be expected to be tetracycline-resistant and auxotrophic, requiring both aromatic metabolites (because of loss of function of gene aroA) and serine plus pyridoxine (because of loss of function of gene serC) as a result of insertion of transposon Tn10 into the chromosome in the promoterproximal part of the serC, aroA operon. After purification, tetracycline-resistant transductants were tested for nutritional character to see if they had acquired the expected requirements. The Aro− SerC− transductant rom the CDC10-80 parental strain was designated 511Ty.

The 511Ty tranductant was used as a recipient in a second transduction, using phage lysate G2013 grown on S. typhimurium SL5253, which has deletion DEL407 extending from within transposon Tn10 inserted at aroA554:Tn10 "rightwards" so as to remove the tetracycline-resistance gene of the transposon, one of its two constituent IS10 elements, and the adjacent portion of gene aroA which includes the sites of aro point mutations 1, 89, 102, 55, 46, and 30, all of which can recombine with each other to produce aro+ and so define different sites in gene aroA. The desired transductants would be expected to have a deletion of part of aroA, but with normal serC function, therefore requiring aromatic metabolites but not serine or pyridoxine. Transductant clones found still exacting for aromatic metabolites but tetracycline-sensitive and not requiring serine or pyridoxine were inferred to have arisen by replacement of the aroA(serC)::Tn10 of the recipient by the serC+ aroA deletion of the donor. The transductant derived from 511Ty was designated 515 Ty.

Introduction of a histidine requirement as marker.

The first donor strain used was strain SL5173, which is S. typhimurium hisD8557:: Tn10 having TN10 inserted in gene hisD and causing inability to effect the last step in histidine biosynthesis and a requirement for histidine not satisfied by provision of histidinol. Lysate G2023 from phage grown on strain SL5173 was applied to S. typhi strain 515Ty having the aroA deletion as described above. Tetracycline-resistant transductants were selected, and, after purification, tested for nutritional character. A clone with a histidine requirement not satisfied by provision of histidinol was selected and designated 521Ty.

The transductant was then treated with phage lysate G1715 grown on S. typhimurium strain hisG46 having a mutation in a gene of the his (histidine-biosynthesis) operon other than hisD, thus providing a requirement for histidine which can be satisfied by provision of histidinol. Selection was made on defined medium supplemented with cystine and aromatic metabolites, together with histidinol (100 μg/ml). A transductant requiring aromatic metabolites as well as either histidine or histidinol was designated 523Ty.

Introduction of purA deletion.

Strains SL5475 and SL5505 are both S. typhimurium LT2 purA155Δzjb-908::Tn10 derivatives of S. typhimurium strain LT2 having a deletion mutation (purA155) within gene purA and having transposon Tn10 inserted at a silent locus (zjb-908) close enough to purA to allow ca. 80% co-transduction of purA155 with zjb-908::Tn10 when transducing phage P22 HT105/1 int grown on strain SL5475 or strain SL5505 is applied to a tetracycline-sensitive pur+ S. typhimurium recipient. Strain SL5475 was constructed by the standard method (Kleckner et al. (1977) J. Mol. Biol. 116:125) for procuring a transposon insertion at a chromosomal site close to a gene of interest, as follows. Strain LT2 purA155 (known to have a deletion of part of gene purA) was treated with transducing phage grown on a pool of several thousand tetracycline-resistant clones, each resulting from an independent insertion of transposon Tn10 at some point in the chromosome of a wild-type strain of S. typhimurium. Several hundred tetracycline-resistant transductants thus evoked from strain purA155 were screened to detect any which had become purine-independent. One such clone was found and designated SL5464. It was believed to have incorporated a transduced chromosomal fragment including gene purA+ and an adjacent Tn10 insertion. By the convention which indicates approximate chromosomal location of insertions, this strain was labelled zjb-908::Tn10. A transducing phage lysate of strain SL5464 (LT2 purA+ zjb-908::Tn10) was next used to evoke tetracycline-resistant transductants from strain LT2 purA155. Of twelve tetracyclineresistant clones thus obtained, only three were purinedependent like their parent. They were believed to result from incorporation of a transduced zjb-908::Tn10 without incorporation of the adjacent purA+ gene of the donor. One of these three clones, of constitution purA155 zjb-908::Tn10, was designated SL5475, and used as donor of the two closely linked genes.

To introduce the purA155 deletion into 523Ty, a phage lysate of strain SL5475 was applied to the tetracycline-sensitive S. typhi recipient strain and selection made for tetracycline-resistant transductants by the same procedure as described above for introduction of the aroA(serC)::Tn10 mutation. After single-colony reisolation, tetracycline-resistant transductant clones were tested for adenine requirement (in addition to their previous requirements for aromatic metabolites and histidine). A purA155 deletion zjb906::Tn10 transductant was obtained and designated 531Ty.

Removal of tetracycline resistance.

Tetracycline-sensitive mutants of 531Ty were obtained by spreading a diluted broth culture on a medium which hinders the growth of strains which are tetracycline-resistant because of presence of Tn10 (Bochner et al. (1980) J. Bacteriol. 143:926). This medium was modified by addition of 2,3-dihydrobenzoic acid, at about 1 μg/ml, because of the aro defect of the S. typhi strain in use. The tetracycline-sensitive mutants thus obtained, resulting from deletion of the part of the transposon causing tetracycline-resistance, were checked to confirm that they were of unaltered nutritional character and that they had the antigenic characters of their S. typhi wild-type ancestor. One such isolate, designated 541Ty, constitutes a Vi-positive aro(deln.) his purA(-deln.) tetracycline-sensitive live-vaccine strain in the CDC10-80 line.

Preparation of aro$^-$ pur$^-$ Vi$^-$ strains.

Vi-negative mutants are obtained from 531Ty by streaking from colonies of phage-resistant mutant bacteria developing in areas of lysis caused by application of Vi phage I, II(adaptation A or E1) or IV, or a mixture of all four of these phages. The phage-resistant mutants, after single-colony reisolation were tested for presence or absence of Vi antigen by slide agglutination tests using commercially available anti-Vi serum and by testing for sensitivity to each of the Vi-specific phages. A mutant scoring Vi-negative in both tests, and retaining its parental nutritional character and ancestral 0 antigenic character was designated 543Ty, and constituted as a Vi-negative live-vaccine strain.

Both 541Ty and 543Ty were fed to volunteers with generally satisfactory results. There were no ill effects on any volunteer and some volunteers showed serological evidence of immune response. In addition, some volunteers excreted the vaccine strain for a day or two demonstrating at least short term viability.

Clements and El-Morshidy, Infect. Immun. (1984) 46:564-569, report the preparation of the plasmid pJC217 containing the gene for expression of the 56kD B region of the heat-labile enterotoxin operon of E. coli. The plasmid pJC217 is transformed into the strains 541Ty and 543Ty as described in Clements and El-Morshidy, supra. The expression of LT-B is confirmed by an ELISA assay. Microtiter plates are precoated with 7.5μg/well of mixed gangliosides (Type III), then with 1 μg per well of purified LT-B. Reagents and antisera are available from Sigma Chemical Co. The samples are serially diluted in PBS(pH 7.2)-0.05% Tween-20. Ampicillin resistant colonies are tested for LT-B. The LT-B positive transformants are then used for immunization for both S. typhi and heat-labile enterotoxin as described previously.

The subject procedure can be used with a wide variety of pathogenic organisms by employing the appropriate transposon to achieve aro$^-$ or other mutant derivatives. Other organisms of particular interest are Escherichia, particularly E. coli, Klebsiella particularly K. pneumoniae, or Shigella. By employing an appropriate transposon which is inserted into an appropriate aromatic-biosynthesis gene, techniques such as transduction with an appropriate general transducing phage e.g. P1, can be employed to provide for aro$^-$ or other mutant non-virulent pathogenic organisms, which are non-revertant.

Although the foregoing invention has been described in some detail by way of illustration and example for purposes of clarity of understanding, it will be obvious that certain changes and modifications may be practiced within the scope of the appended claims.

What is claimed is:

1. A method for preparing a live non-virulent vaccine from a virulent pathogenic bacterium, which vaccine is substantially incapable of reverting to virulence in a vertebrate host susceptible to infection with said bacterium while providing for a strong immune response, said method comprising:
   (a) transducing cells of an immune response producing strain of said microorganism with a first transducing phage having at least a portion of a first gene, which first gene expresses a protein in a first biosynthetic pathway to a first essential metabolite normally unavailable in said vertebrate host, and which gene includes a non-reverting mutation, resulting in a culture of a first auxotrophic non-cirulent mutant;
   (b) selecting for said auxotrophic mutant by means of said first auxotrophic mutation or other marker introduced by transduction;
   (c) transducing said first auxotrophic mutant with a second transducing phage having at least a portion of a second gene, which second gene expresses a protein in a second biosynthetic pathway to a second essential metabolite normally unavailable in said vertebrate host, and which second gene includes a non-reverting mutation, resulting in a culture of a second auxotrophic non-virulent mutant;
   (d) selecting for said second auxotrophic mutant by means of said second auxotropphic mutation or other marker introduced by transduction;
   (e) isolating said second auxotrophic non-reverting mutant transductants;
   (f) introducing an expression cassette containing a DNA sequence encoding an antigen foreign to said pathogenic bacterium, under regulatory control of regulatory regions recognized by said pathogenic basterium, into said pathogenic basterium, first mutant, or second mutant to produce a transformed hose cell;
   (g) growing said transformed hose cell; and
   (h) identifying and isolating transformed host cells expressing said antigen;
   wherein (f), (g), and (h) may be carried out before or after any one of (a) through (e), resulting in a culture of auxotrophic, non-reverting, non-virulent mutant bacteria capable of expressing an antigen foreign to said bacteria.

2. A method according to claim 1, wherein said antigen is a membrane protein.

3. A method according to claim 1, wherein said antigen is a bacterial protein.

4. A live Salmonella cell having a requirement for aromatic metabolites and adenine as a result of non-reverting deletions, and expressing an antigen of a pathogen other than Salmonella as a result of introducing into said cell an expression cassette comprising an DNA sequence encoding said antigen under regulatory control of regulatory regions recognized by said cell.

5. A live Salmonella cell according to claim 4 which is aroA$^-$ and purA$^-$.

6. A live Salmonella cell according to claim 4 of the species *typhimurium*.

7. A live Salmonella cell according to claim 4 of the species *dublin*.

8. A live Salmonella cell according to claim 4 of the species *typhi*.

9. A vaccine comprising live Salmonella cells according to claim 4 in an amount and at a concentration to provoke an immune response with a physiologically acceptable carrier.

10. A vaccine according to claim 9, wherein said Salmonella cells are *typhimurium, dublin* and/or *typhi*.

11. A vaccine according to claim 10, wherein said cells are capable of expressing an antigen of a pathogen other than Salmonella.

12. A method for preparing a live non-virulent vaccine from a virulent pathogenic bacterium, which vaccine is substantially incapable of reverting to virulence in a vertebrate host susceptible to infection with said bacterium while providing for a strong immune response, said method comprising:
(a) mutating an immune response producing strain of said pathogenic bacterium to produce at least one of a deletion or inversion non-reverting mutation of a first gene, said first gene expressing a protein in a first biobynthetic pathway to a first essential metabolit normally unavailable in said vertibrate hose, resulting a culture of a first auxotrphic non-cirulent mutant;
(b) selecting for said first auxotrophic mutant;
(c) mutating said first auxotrophic mutant to produce at least one of a deletion or inversion non-reverting mutation in a second gene, which second gene expresses a protein in a second biosynthetic pathway to a second essential metabolite normally unavailable in said vertebrate hose, resulting in a culture of a second auxotrophic non-virulent mutant;
(d) selecting for said second auxotrophic mutant;
(e) isolating said second auxotrophic non-reverting mutant to provide an living vaccine;
(f) introducing an expression cassette containing a DNA sequence encoding an antigen foreign to said pathogenic bacterium, under regulatory control of regulatory regions recognized by said pathogenic bacterium, into said pathogenic bacterium, first mutant, or second mutant to produce a transformed host cell;
(g) growing said transformed host cell; and
(h) identifying and isolating transformed host cells expressing said antigen;
wherein (f), (g) and (h) may be carried out before or after any one of (a) through (e), resulting in a culture of auxotrophic, non-reverting, non-virulent mutant bacteria capable of expressing an antigen foreign to said bacteria.

13. A method according to claim 12, wherein said first gene and second gene are different members of the group aro, pur or pab genes.

14. A method according to claim 13, wherein said first and second genes are the aro gene and the pur gene.

15. A method for preparing a live attenuated vaccine from virulent pathogenic bacteria, which vaccine has a substantaily zero probability of reverting to virulence in a vertebrate host, said method comprising:

isolating auxotrophic, non-reverting, non-virulent mutant bacteria wherein said mutant bacteria are obtained by blocking a biosynthitic pathway of a metabolite essential for multiplication of said pathogenic bacteria and normally unavailable in said vertebrate host, wherein said mutant bacteria are prepared by a method comprising:
(a) transducing cells of said pathogenic bacteria with a transducing phage comprising at least a portion of a gene expressing a protein in said biosynthetic pathway, wherein said gene includes a non-reverting mutation, resulting in a culture of auxotrophic, non-reverting, non-virulent mutant bacteria; and
(b) introducing a transposon into a gene of said pathogenic bacteria, wherein said gene expresses a protein in said biosynthetic pathway and wherein said transposon provides a phenotypic property allowing for selection of the presence of said transposon; selecting for bacteria having said phenotypic property provided by said transposon and isolating transposon-modified bacteria; and selecting for, from said transposon-modified bacteria, bacteria lacking said phenotypic property due to excision of all or a part of said transposon and being auxotrophic due to a non-reverting mutation in said gene as a result of said excision;
wherein (a) and (b) may be carried out in any order resulting in a culture of auxotrophic, non-reverting, non-virulent virulent bacteria.

16. The method according to claim 15, further comprising:
(c) introducing an expression cassette containing a DNA sequence encoding an antigen foreign to said pathogehic bacterium, under regulatory control of regulatory regions recognized by said pathogenic bacterium, into said pathogenic bacterium or said mutant bacteria selected in (a) or (b) to produce a transofred host cell;
(d) growing said transformed host cell; and
(e) identifying and isolating transformed host cells expressing said antigen;
wherein (c), (d) and (e) may be carried out before or after any one of (a) and (b), resulting in a culture of auxotrophic, non-reverting, non-virulent mutant bacteria having the further characteristic of being capable of expressing an antigen foreign to said pathogenic bacteria.

* * * * *